United States Patent [19]

Kindle et al.

[11] Patent Number: 4,600,693

[45] Date of Patent: Jul. 15, 1986

[54] THERMOSTABLE ALPHA AMYLASE HAVING A LOW REQUIREMENT FOR CALCIUM IONS, DERIVED FROM A BACILLUS MICROORGANISM

[75] Inventors: Karen L. Kindle, Brooktondale, N.Y.; Stanley E. Mainzer, Burlingame, Calif.; Deborah L. Marlatt, Painted Post; Constance B. Sawyer, Lindley, both of N.Y.

[73] Assignee: Corning Glass Works, Corning, N.Y.

[21] Appl. No.: 579,773

[22] Filed: Feb. 13, 1984

[51] Int. Cl.$^4$ ............... C12N 11/14; C12N 11/02; C12N 9/28; C12N 1/20; C12R 1/07
[52] U.S. Cl. ............................ 435/176; 435/177; 435/202; 435/253; 435/832
[58] Field of Search ................ 435/202, 253, 176, 177

[56] References Cited

U.S. PATENT DOCUMENTS 4,284,722 8/1981 Tamuri et al. .
4,473,645 9/1984 Horwath ........................... 435/202

OTHER PUBLICATIONS

K. Ogasahara et al., The Journal of Biochemistry, vol. 67, No. 1, 1970, pp. 65, 77, 83.
Manning et al., The Journal of Biological Chemistry, vol. 236, No. 11, Nov. 1961, pp. 2952, 2958, 2962.

*Primary Examiner*—Lionel M. Shapiro
*Attorney, Agent, or Firm*—Brian D. Voyce

[57] ABSTRACT

The present invention relates to a novel thermostable alpha amylase having a low requirement for calcium ions, and a novel Bacillus microorganism that produces it extracellularly. This amylase is useful in high temperature, low calcium applications, e.g., in detergent compositions.

4 Claims, 12 Drawing Figures

THERMOSTABLE ALPHA AMYLASE HAVING A LOW REQUIREMENT FOR CALCIUM IONS, DERIVED FROM A BACILLUS MICROORGANISM

TECHNICAL FIELD

The present invention relates to a novel thermostable alpha amylase having a low requirement for calcium ions, and a novel Bacillus microorganism that produces it extracellularly. This amylase is useful in high temperature, low calcium applications, e.g., in detergent compositions.

BACKGROUND ART

Alpha amylases are available from many microorganisms living in diverse environments Bacterial sources include *Bacillus subtilis, Bacillus licheniformis,* and *Bacillus stearothermophilus*. It should be noted that although each of these sources can yield a thermostable amylase, the enzymes differ substantially in characteristics such as molecular weight, pH optimum, temperature optimum, and calcium ion affinity. In other words, the enzymes from these sources are conveniently grouped together because they hydrolyze starch into malto-dextrins.

U.S. Pat. No. 4,284,722 to Masaki Tamuri, Mitsuo Kanno, and Yoshiko Ishii describes a particular heat and acid-stable amylase made by a *Bacillus stearothermophilus* organism. The enzyme is characterized as having a pH optimum of about 4 to 6, a temperature optimum of about 65° to 85° C., and a molecular weight of about 90,000.

The Bacillus organism of Tamuri et al. is deposited in the American Type Culture Collection (ATCC) as *Bacillus stearothermophilus* strains Nos. 31,195–31,199. Other alpha amylases from *Bacillus stearothermophilus* are reported by Ogasahara et al., J. Biochem, (1970), 67, pp. 65, 77, 83 and Manning et al., J. Biol Chem, (1961) 236, pp. 2952, 2958, 2962.

DISCLOSURE OF THE INVENTION

The present invention relates to isolated cultures of a novel Bacillus bacterium. When cultured in a suitable nutrient medium, it produces an extracellular, thermostable alpha amylase which has a high affinity for calcium ions.

Bacterium

The instant bacterium has been identified as a novel *Bacillus stearothermophilus* ( st. ). It is referred to as such due to a lack of another genus within which it can be classified. The present organism has been deposited in the American Type Culture Collection under accession number 39,536.

The taxonomic properties of the present *Bacillus st.* are shown in the following table:

| A. Morphological Characteristics | | |
|---|---|---|
| 1. | Rods | 0.40 to 0.50 μm in diameter |
| | | 1.60 to 4.80 μm in length |
| | Gram-negative | |
| 2. | Flagella and endospores - (Non motile) no flagella, terminal endospores are formed. | |
| B. Carbohydrate Utilization | | |
| (Culture Conditions) - Brock's Medium and 0.5% BHI | | |
| | Arabinose - acid | − |
| | gas | − |
| | Glucose - acid | + |
| | gas | − |
| | Lactose - acid | + |
| | gas | PG |
| | Mannitol - acid | + |
| | gas | − |
| | Sucrose - acid | + |
| | gas | − |
| | Xylose - acid | − |
| | gas | − |

PG = Poor Growth
+ = Growth
− = No Growth

| C. Physiology - | | |
|---|---|---|
| Medium | | |
| Anaerobic Gas From NO$_3$ broth | | + |
| Litmus Milk 7 days | | − |
| Litmus Milk 14 days | | Reduced |
| NaCl broth (0%) | | + |
| NaCl broth (5%) | | − |
| Citrate | | + |
| Proprionate | | + |
| Azide Glucose | | − |
| Egg Yolk Reaction | | − |
| Starch Hydrolysis | | + |
| Hippurate Hydrolysis | | + |
| Gelatin Hydrolysis | | − |
| Casein Hydrolysis | | − |
| Tyrosine Decomposition | | Weak |
| Catalase | | + |
| Potassium Nitrate Reduction (KNO$_2$) | | + |
| Potassium Nitrate Reduction (Gas) | | − |
| Dihydroxyacetone | | − |
| Indole | | − |
| Voges-Proskauer Methylene Blue | | + |
| Voges-Proskauer Methylene Blue (pH) | | 7.0 |
| + = Positive Reaction | | |
| − = Negative Reaction | | |
| E. Relation to Oxygen - | Obligately Aerobic | |
| F. Relation to pH - | (optimum) | 5.5 to 7.5 pH (15° C.) |
| | | 4.5 to 7.5 pH (60° C.) |
| G. Relation to Temperature - | (optimum) | 70 to 75° C. |
| | (limits) | 40 to 80° C. |

The culture media used above are all known to those of skill in the art.

Enzyme

The present *Bacillus st.* makes a novel and especially useful alpha-amylase when cultured in a simple salts medium at temperatures of 50° to 55° C. and pHs of 6.5 to 7.5. The amylase metabolite is highly thermostable and has a low requirement for calcium ion concentration, i.e. high affinity for calcium ions.

These characteristics are useful because they are exhibited by the instant amylase even when present in a commercial detergent composition. Full activity and stability do not require calcium ion concentrations required by other amylases, thereby allowing the use of softer (less calcium ion containing) water or the presence of chelators in the detergent.

Using 80% activity as the minimum, the present amylase has a temperature optimum of 60° to 87° C. at pH 7.0, and a p H optimum of 5.3 to 7.5 at 75° C. In both cases 5mM CaCl$_2$ was present. Perhaps even more revealing, both these low calcium ion concentrations and throughout a very broad range of temperatures 4 to 75° C., the enzyme is more stable than other known amylases.

One way of harvesting or using the present amylase is to immobilize either the enzyme or the present bacterium on an insoluble carrier. The immobilized bacterium will produce the desired amylase as an extracellular metabolite which can be readily harvested.

On the other hand, immobilizing the enzyme would enable one to economically use it for starch hydrolysis. Suitable carriers include glasses, ceramics, and organic polymers. Suitable immobilization or attachment methods include adsorption, crosslinking, entrapment and bonding. Both the immobilized enzyme and bacterium should be kept in a suitable environment, i.e. pH, temperature, oxygen, and, for the bacterium, nutrients. These are conventional materials and techniques known to those of ordinary skill in the art.

Other conventional enzyme recovery methods for extracellular enzymes are well known to the art.

MODES FOR CARRYING OUT THE INVENTION

Culturing the Organism

Cells from the present Bacillus st. strain were grown in Brocks's medium [Brock, T.D. (1978) *Thermophilic Micoorganisms and Life at High Temperatures,* Springer-Verlag, NY], 0.2% Brain Heart Infusion and 0.5% starch. Culture times and temperatures range, respectively, from 48 to 72 hours and 55° to 77° C. Alpha-amylase was produced extracellularly during the growth phases. Typically, the stationary phase of growth was reached after 48 hours, and further incubation did not increase the amount of extracellular enzyme greatly.

Preparing the Amylase

After a culture of the instant *Bacillus st.* had reached the stationary growth phase, the cells were removed by centrifugation. The remaining supernatant was concentrated and dialyzed at pH 7.0 against a 50 mM 3-[N-Morpholino]propanesulfonic acid (MOPS) buffer, thereby producing the amylase concentrate. (The equipment used was an Amicon pressure filtration unit having a PM-10$^{TM}$ membrane with a 10 K molecular weight cutoff.) The enzyme was treated with sodium azide (to 0.02%) and stored at 4° C.

Assaying Amylase Activity

Two different assays were used for amylase activity. In the first, the ability of starch to be stained blue by iodine was used in a modification of the Fuwa method, as described by Robyt, N. F. and Whelan, W. J., the α-Amylases, in *Starch and Its Derivatives,* (1968) Radley, J. A., ed, Chapman and Hall, London, pp. 430–476. Units were calculated as described by these authors, and are related to the fractional decrease in blue staining per ml of enzyme. The pH (buffer) and temperature for the assay were altered as described in Figure legends.

The second assay was the colorimetric, Nelson reducing-sugar assay essentially as described by Robyt and Whelan (5), see above. The assay was performed as follows: 100 μl of appropriately diluted enzyme was added to 1.9 mls. of preheated substrate. The reaction was generally incubated for 10 minutes at the indicated temperature, stopped by the addition of 1 ml of Nelson Reagent D and carried through the rest of the assay as described. Instead of using a boiling water bath, a 95°–100° C. Fisher Isotemp heat block was used to develop color.

Unless otherwise indicated the assays were incubated in 50 mM buffer (usually MOPS at pH 7.0) 5 mM $CaCl_2$, 0.5% starch at 75° C. Units are expressed as μmoles of maltose reducing equivalents produced per minute under the conditions stated.

Growth Rate

Figure 1:
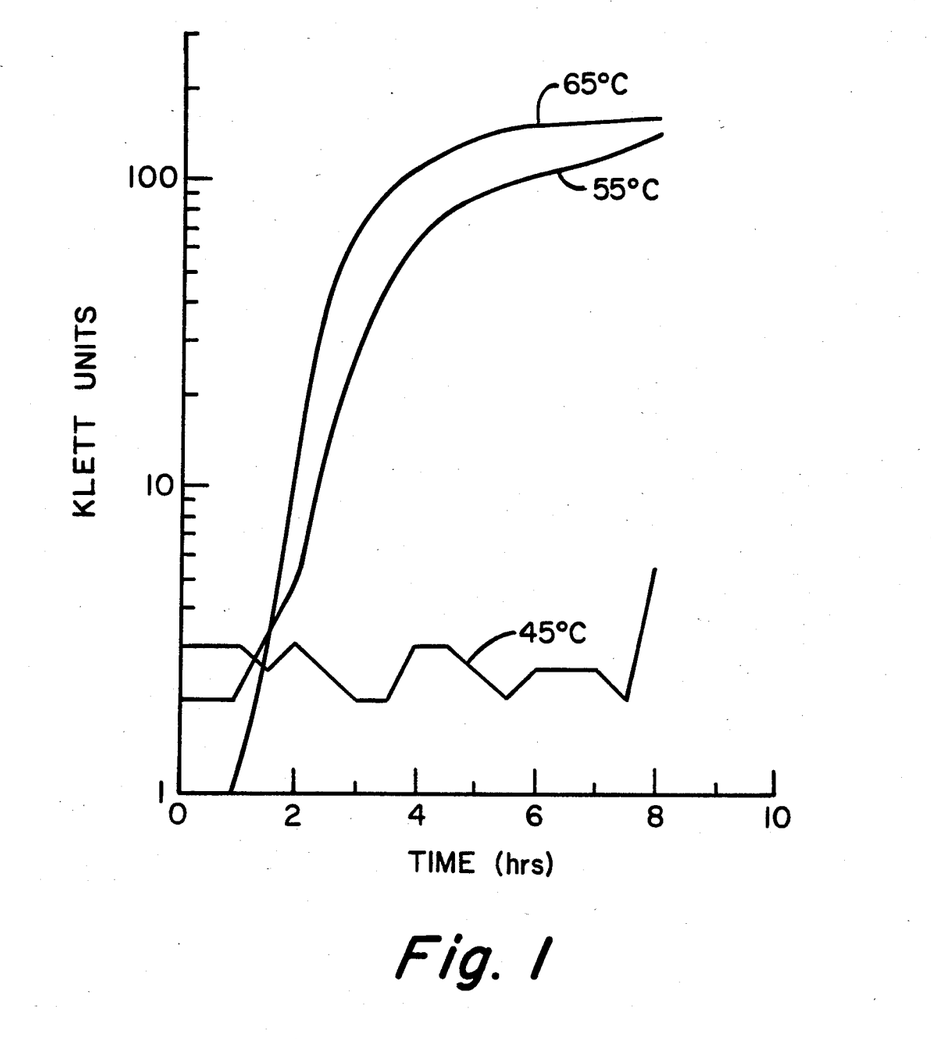
FIG. 1 is a graph of the effect of temperature on the growth of the present Bacillus organism.

FIG. 1 shows how temperature affected the growth rate of the present *Bacillus st.*. The three cultures had been incubated in the above medium supplemented with 0.05% yeast extract, with noted changes in temperature. The initial doubling times are 18 and 15 minutes for, respectively, temperatures of 55° and 65° C. However, growth at 45° C. occurs only after an extended lag.

Amylase Production

Figure 2:
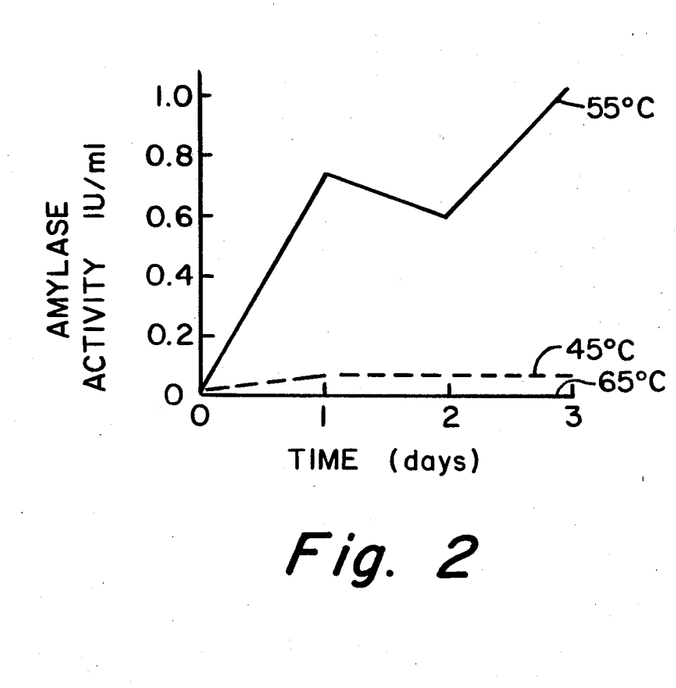
FIG. 2 is a graph of the effect of temperature on amylase production in the first hours of culture.

The effect of temperature on the output of active amylase by growing cultures is shown in FIG. 2. The cultures of FIG. 1 were assayed for amylase by the Nelson method. The results reveal that there is very little active amylase produced at 45° C. and essentially none detected at 65° C. However, in between, at 55° C., there is 1 IU/ml made after one day.

Figure 3:
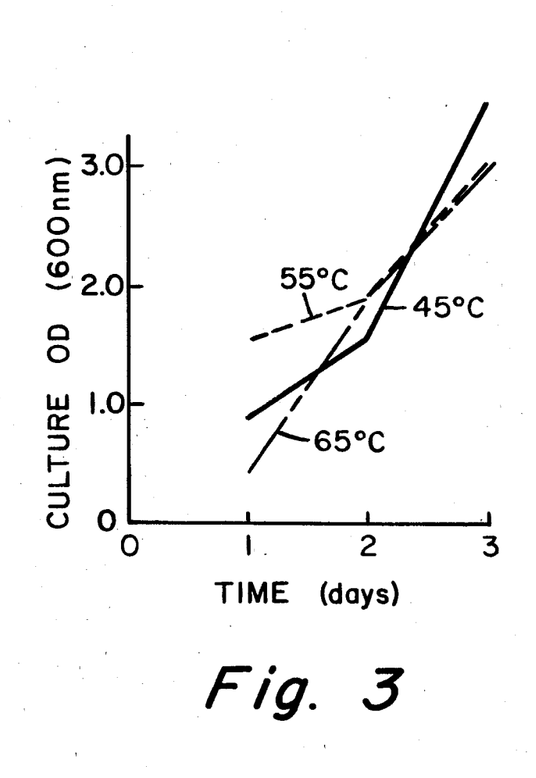
FIG. 3 is a graph of the effect of temperature on amylase production over several days.

To check whether differences in amylase production are due to differing amounts of cell mass, the optical density (OD) of the cultures have been monitored. FIG. 3 shows that the amount of cell mass (as determined by optical density measurements) are similar. Thus, the superior production of amylase at 55° C. is not due to a better growth rate.

Effect of Temperature on the Amylase

The thermostability of the present amylase has been measured by first determining the optimum temperature range for activity, then holding the enzyme in those ranges for 10 minutes and assaying for activity by the Nelso method. As a comparison, a highly thermostable alpha-amylase from *Bacillus licheniformis* (l.) has been tested as well in the above pH 7.0, MOPS buffer. The particular organism is *Bacillus licheniformis* NCIB 8061 from the National Collection of Industrial Bacteria, Torrey Research Station, Aberdeen, Scotland.

Figure 4:
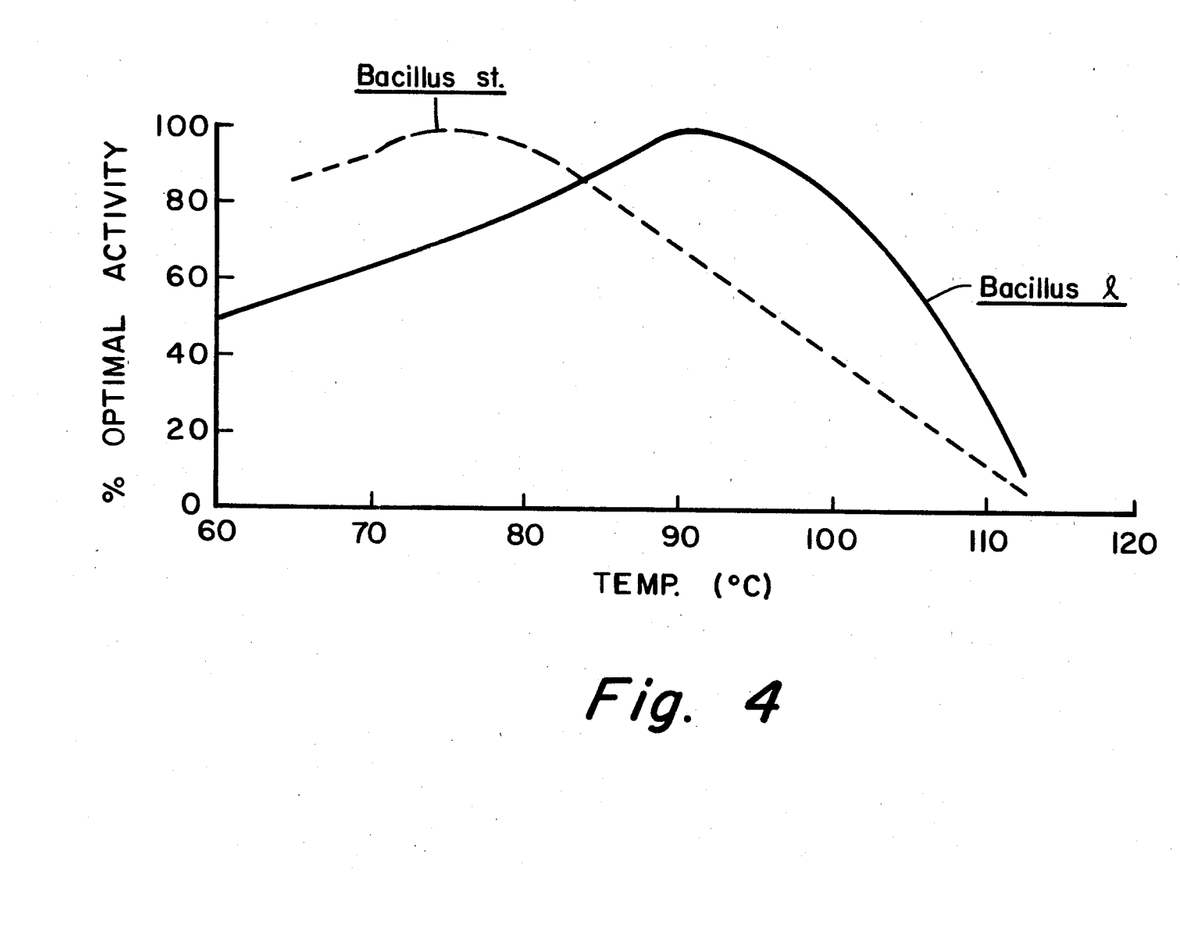
FIG. 4 is a graph of the optimum temperatures for activity in the instant enzyme.

The optimum temperatures ($T_{opt}$) for these amylases in the absence of substrate is disclosed in FIG. 4. *Bacillus l.* has a $T_{opt}$ of 90°–95° C., while retaining 50% activity at 105° C. The present *Bacillus st.* amylase was different, having a $T_{opt}$ of 75° C., and retaining 50% activity at 95° C.

Figure 5:
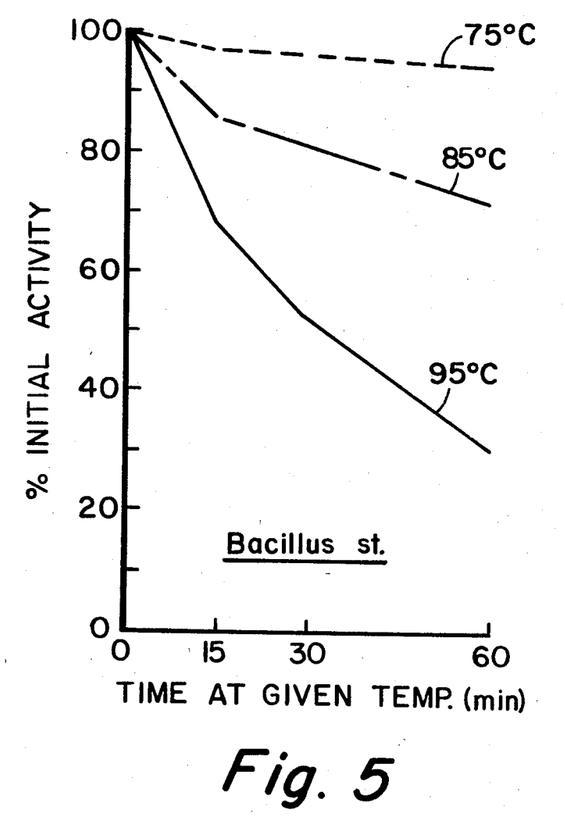
FIG. 5 is a graph of the thermostability of the present amylase.
Figure 6:
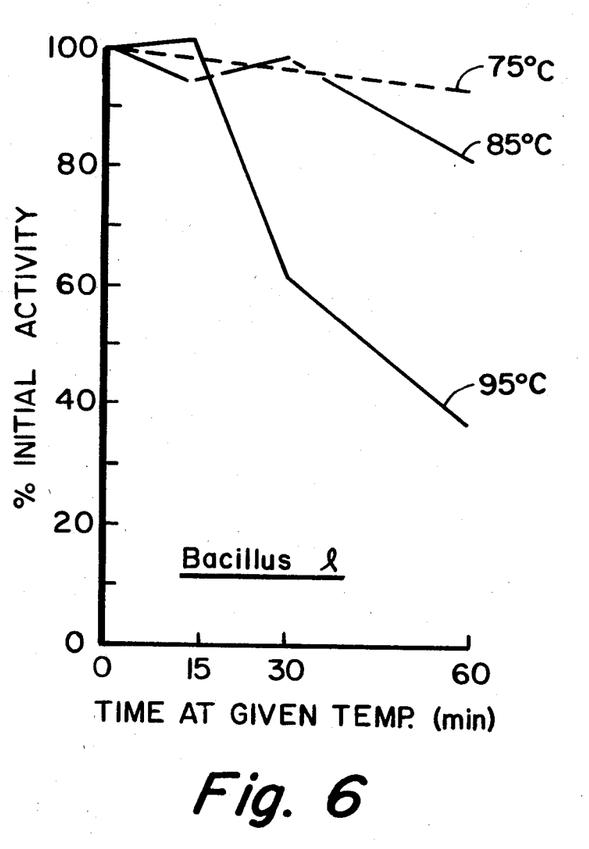
FIG. 6 is a graph of the thermostability of Bacillus l. amylase.

The thermal stability of these amylases have been examined at 75, 85, and 95° C. The buffered enzymes have been held at the respective temperatures for up to an hour. As represented by FIG. 5, the present *Bacillus st.* amylase loses only 5% of its activity after one hour at 75° C., 30% at 85° C., and 70% at 95° C. This is similar to the results for *Bacillus l.* in FIG. 6, i.e., 5, 20, and 60% at, respectively 75, 85, and 95° C.

Substrates often enhance the thermal stability of enzymes, so the activity and stability of *Bacillus st.* and l. amylases in the presence of relatively high concentrations of starch have been compared. Equal amounts of amylase activity (as measured at their optimum temperatures) are added to 20% soluble starch and incubated at 112° C. in sealed serum vials. Samples are taken at various times and assayed by the Nelson method.

Figure 7:
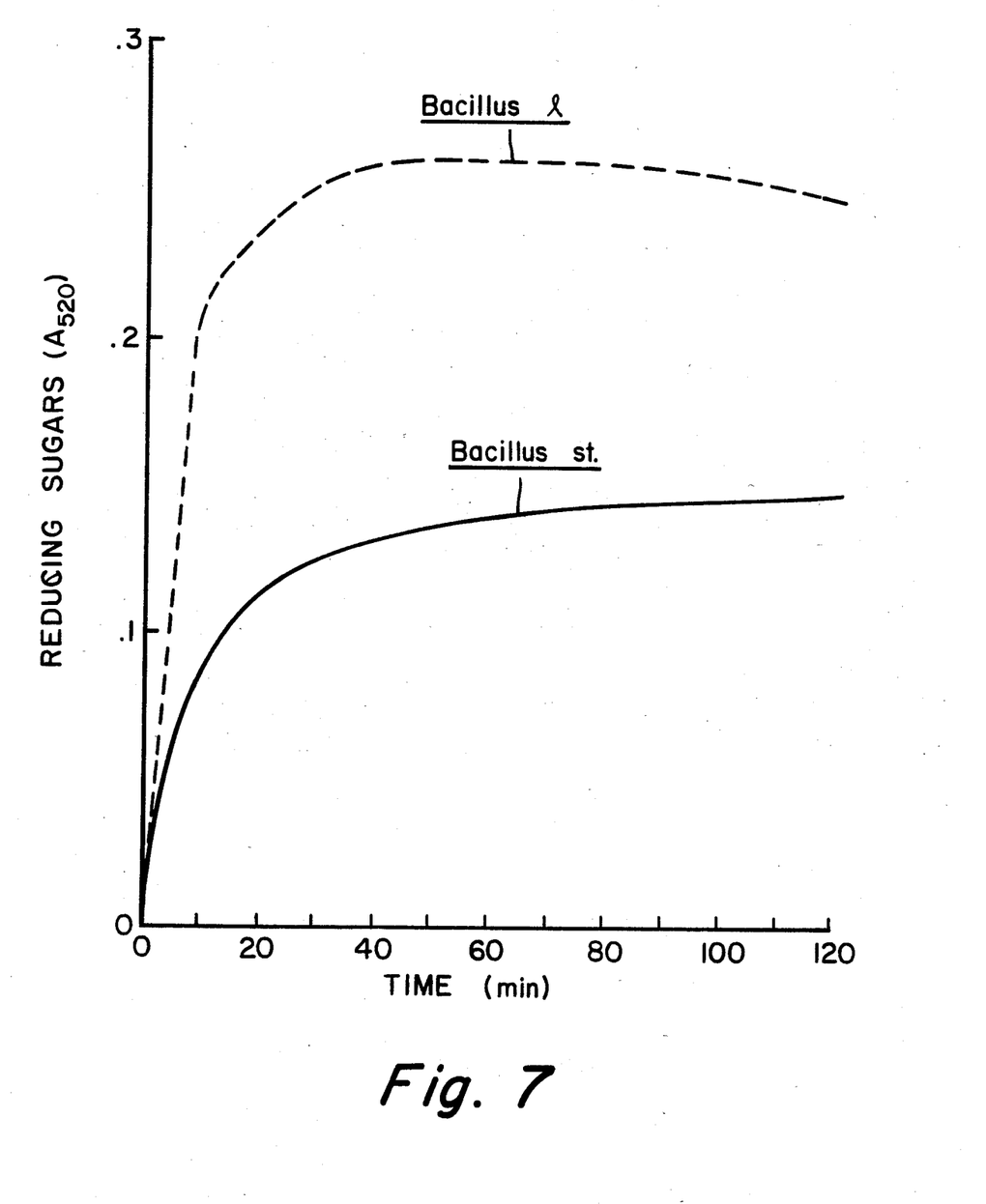
FIG. 7 is a graph of the thermostability of the present amylase and Bacillus l. amylase in high starch concentrations.

The results of the starch comparison are shown in FIG. 7. Although equal amylase activity is used, the Bacillus l. amylase produces almost twice as many reducing ends before it is inactivated. However, the amount of reducing sugar continues to rise for 60 minutes with the present amylase, as opposed to a maximum in 40 minutes for the other enzyme. It is clear that although the present amylase is highly thermostable, it is not as active at extreme temperatures as the *Bacillus l.* amylase.

Effect of pH on the Amylase

The pH stability of the present amylase is measured in a manner slightly different from that for temperature stability. Although the optimum pH range is determined within the optimum temperature range, the stability is tested at room temperature.

More particularly, in two sets of tests, the enzyme is subjected to varying pH buffers (3-11) at two constant temperatures, 60° and 75° C. Activity is assayed by the Robyt and Whelan method. As seen in FIG. 7, there is a broad, optimum pH range of 5-7.5 at 75° C. and 4-7.5 at 60° C.

Figure 8:
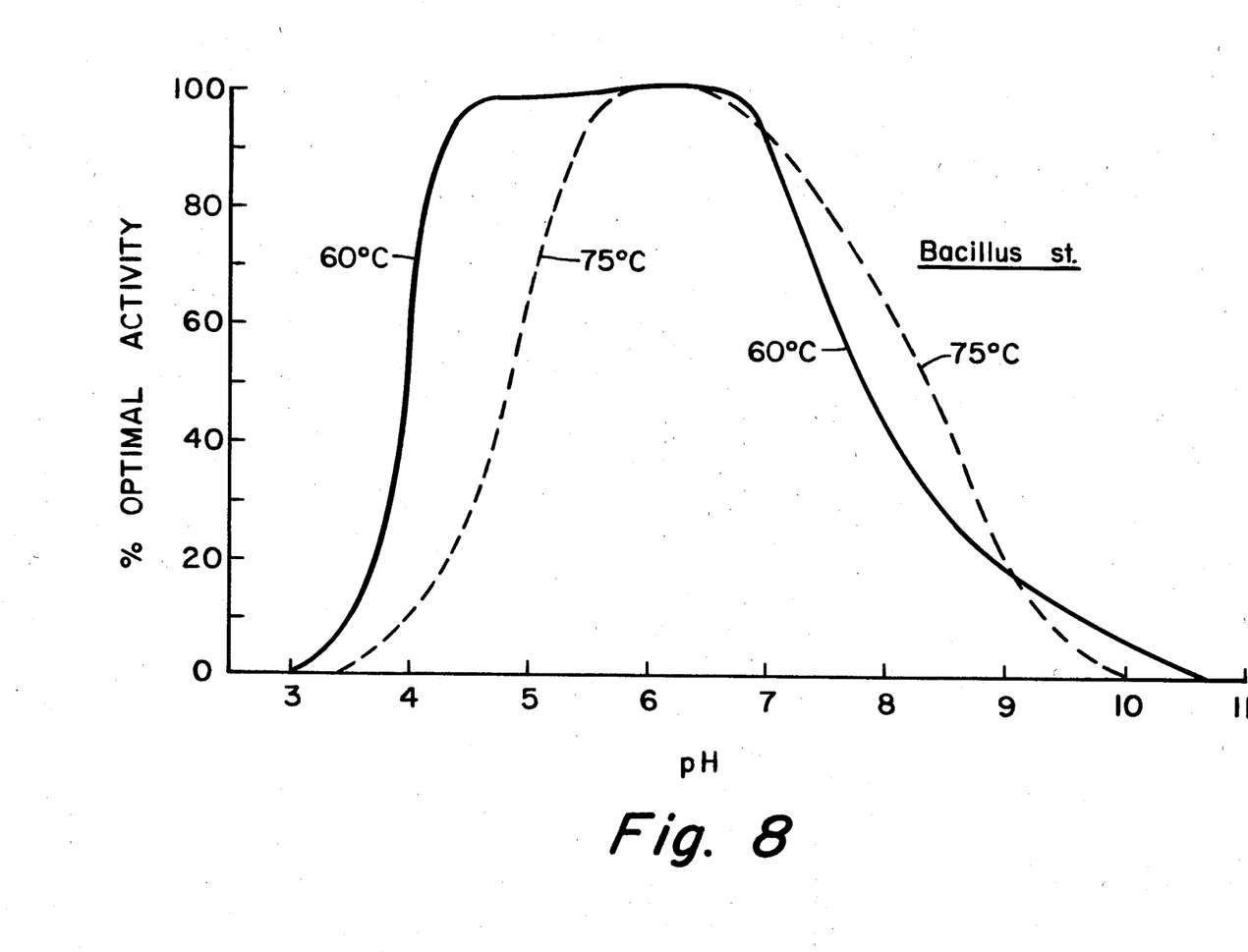
FIG. 8 is a graph of the optimum pH for amylase activity in the present amylase.
Figure 9:
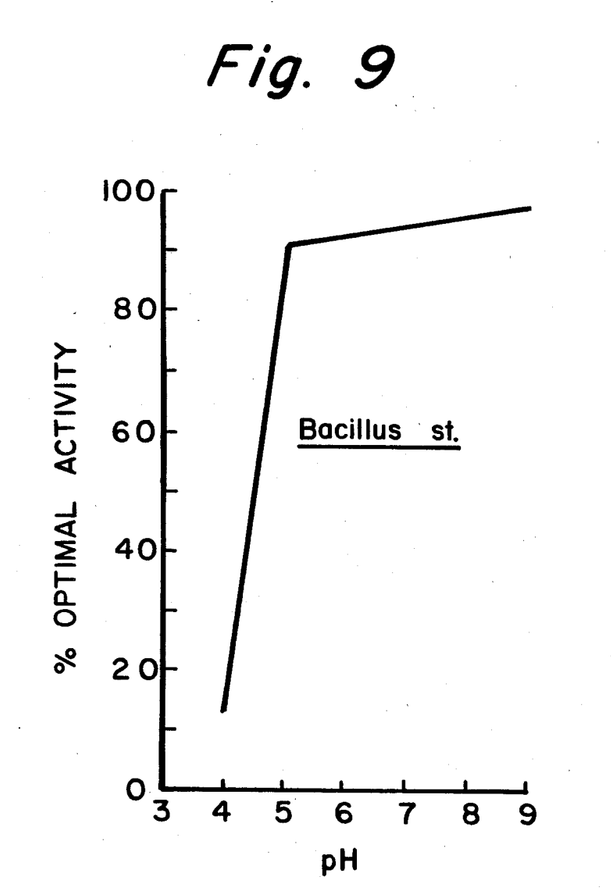
FIG. 9 is a graph of the pH stability of the present amylase.

Testing stability, the present amylase is then held at room temperature for 24 hours, again in a variety of buffers. After this incubation, the samples are tested for residual activity in a pH 7.0 MOPS buffer. FIG. 8 illustrates that the enzyme is stable at pH 5-9, but only 15% of the activity remains at pH 4.

Calcium Affinity of the Amylase

Amylases with relatively low requirements (and thus, a high affinity) for calcium ion are commercially desirable. One way of testing for this property is to measure the thermal stability of an amylase in varying calcium ion concentrations. Accordingly, the *Bacillus st.* and l. amylases have been tested in 0.0-0.5 mM concentrations.

Culture supernatants from the respective organisms are dialyzed for 24 hours against 100 volumes of 1 mM EDTA (changed twice) in a 50 mM MOPS pH 7.0 buffer. Then they are checked for thermostability by holding them at 75° C. for 90 minutes. At 0.0 mM of $Ca^{++}$ and 1 mM EDTA, both enzymes lose all activity within 15 minutes. Therefore, the enzymes are dialyzed extensively against 50 mM MOPS to remove EDTA, and CaCl added back at various concentrations before again checking for thermostability.

Figure 10:
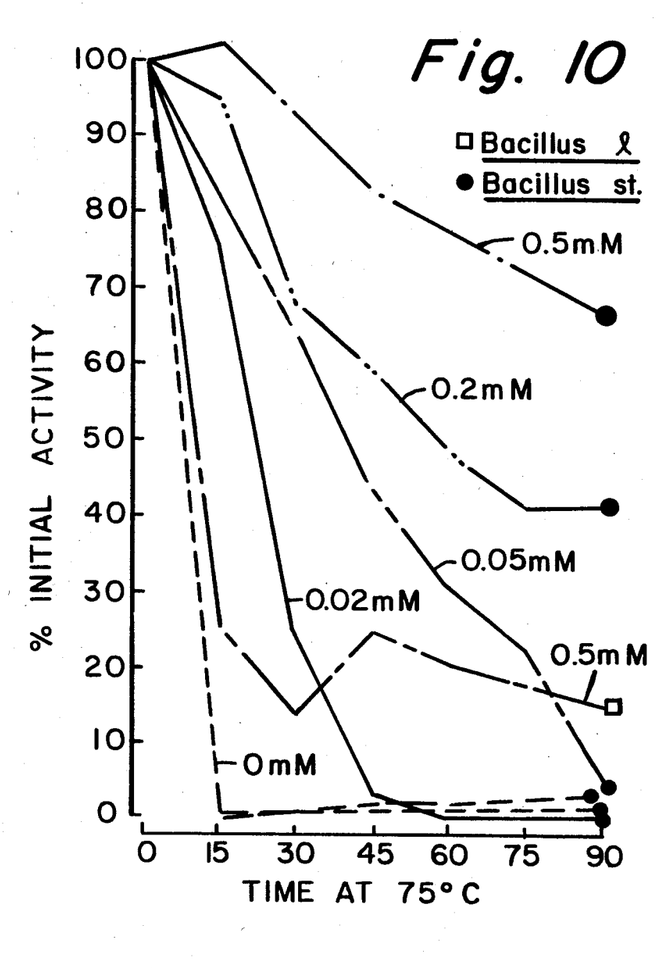
FIG. 10 is a graph of the effect of calcium ion concentration on the present amylase and that of Bacillus l..

FIG. 10 shows that even low levels of $CaCl_2$ (0.02-0.05 mM) protect the present amylase from thermal inactivation. For example, incubation in 0.5 mM $CaCl_2$ results only in a 30% loss of initial activity. Thus, *Bacillus st.* amylase has an even higher affinity (or lower requirement) for calcium ion than *Bacillus l.* amylase which loses 80% of its activity after 30 minutes.

Figure 11:
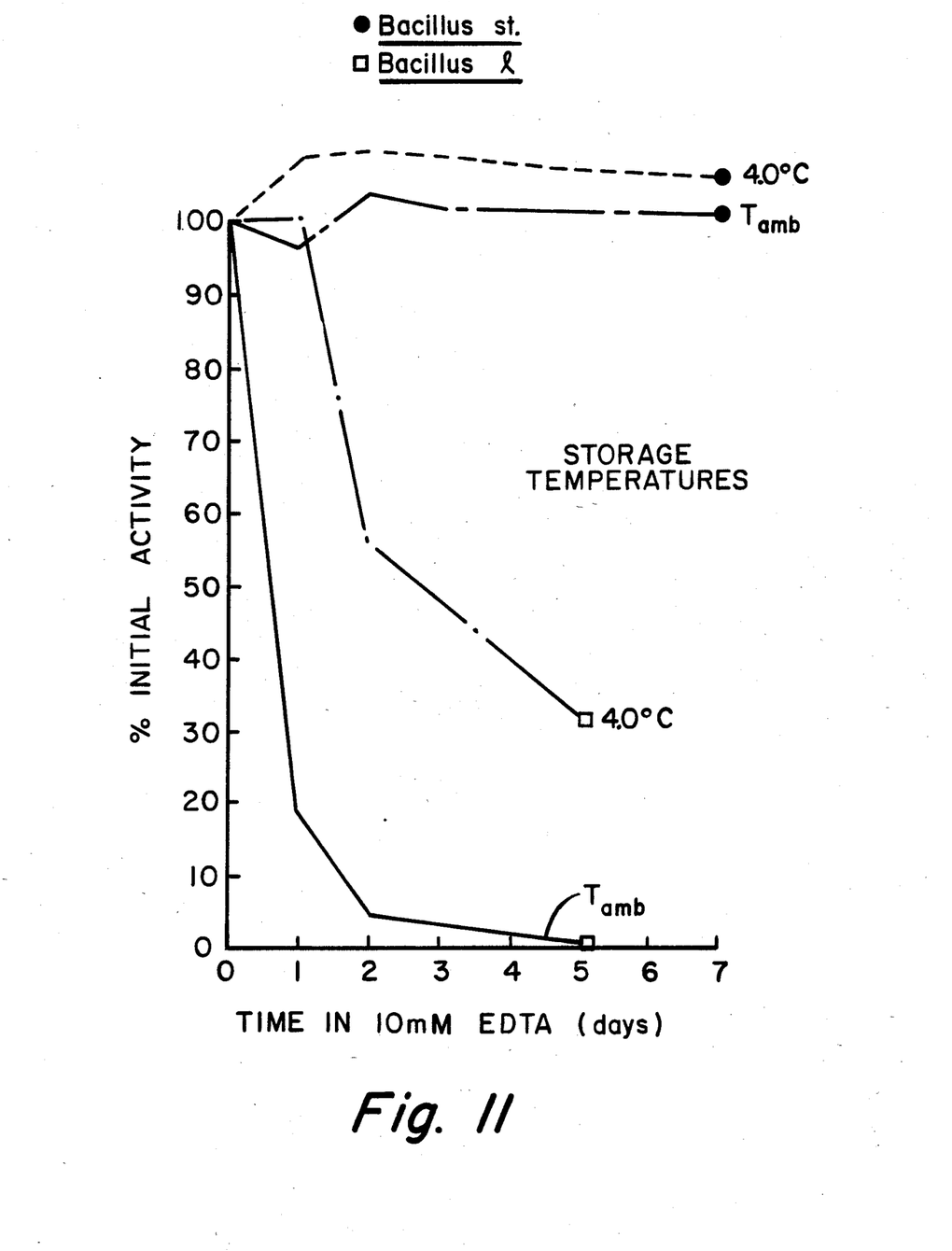
FIG. 11 is a graph of the effect of EDTA storage on the present amylase and that of Bacillus l..

To further understand this observation, the stability of these amylases has been assayed by the Nelson method after storage in 10 mM EDTA at both room temperature ($T_{amb}$) and 4° C. FIG. 11 shows that *Bacillus st.* amylase loses no activity after 7 days in the presence of 10 mM EDTA regardless of temperature. However, in 5 days under the same conditions, the known amylase loses all of its activity at room temperature and 70% at 4° C.

Molecular Weight of the Amylase

The molecular weight of the present enzyme is determined by polyacrylamide gel electrophoresis (PAGE). A Hoefer PAGE system can be used, operated according to conditions recommended by the manufacturer for denaturing sodium dodecyl sulfate (SDS) gels. For example, a small amount of amylase is purified by adsorption to corn starch. About 80% of the activity is adsorbed in 30 minutes at room temperature. Then the starch is extensively washed with cold water. Of this, 40-50% is eluted at 65° C. with a 20 mM MOPS, pH 7.0 buffer. The eluted supernatant proteins and fractions are separated then on SDS-polyacrylamide gels. Electrophoresis is run at 30 mA/mm gel-thickness for 2½ hours.

Figure 12:
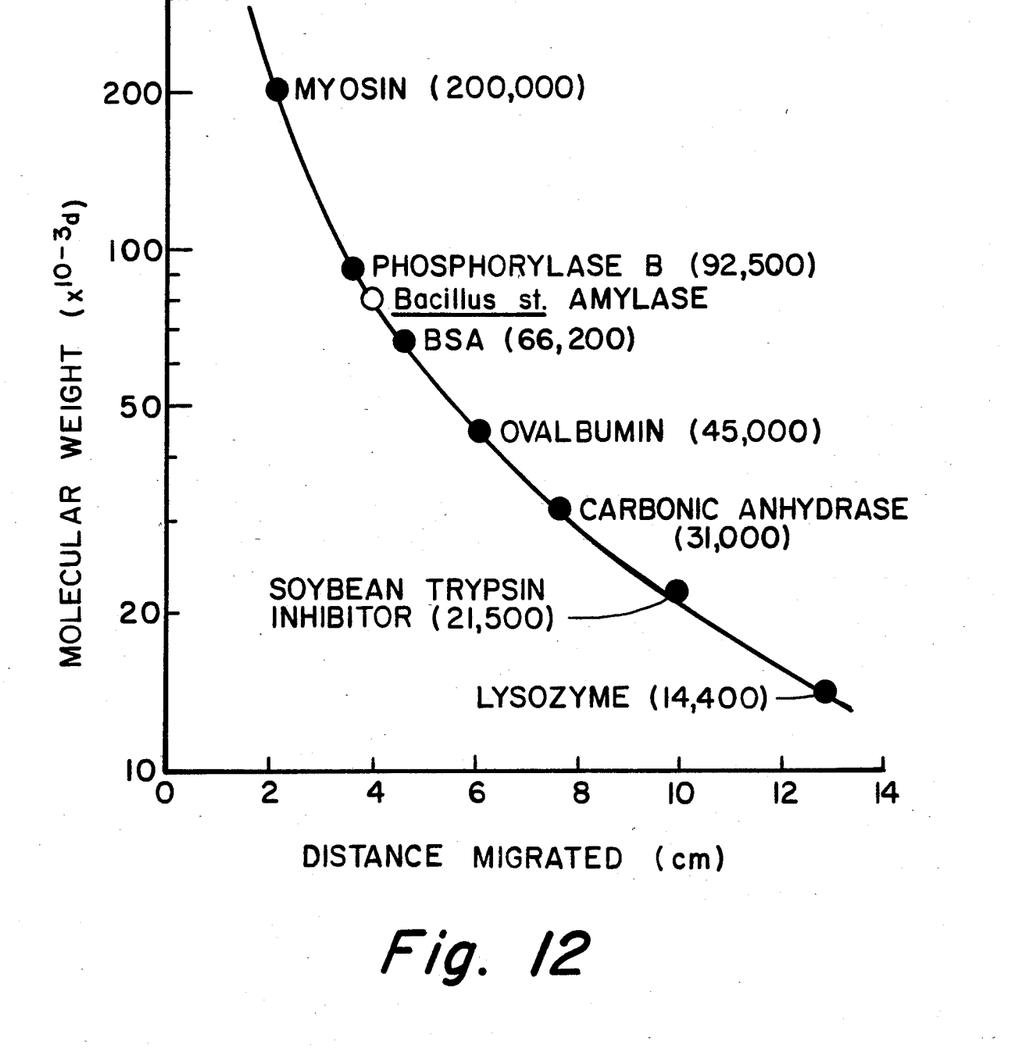
FIG. 12 is a graph showing the molecular weight of the present amylase.

The separated bands are visualized by conventional methods and compared against standard protein markers. As shown in FIG. 12, *Bacillus st.* amylase has a purified band that migrated to a position between phosphorylase B (92.5 K dal) and borine serum albumin (BSA) (66.2 K dal). Thus, the present enzyme has a molecular weight of 80 K dal.

The following table compares the molecular weight of the present novel amylase with other known (*Bacillus st.*) amylases:

| Source | M.W. (K dal) |
| --- | --- |
| Tamuri ATCC No. 31,195 and 31,199 | 96.0 |
| Present Organism ATCC No. 39,536 | 80.0 |
| Ogasawara | 48.0 |
| Manning | 15.6 |

Having described the invention with particular reference to preferred form, it will be obvious to those skilled in the art to which the invention pertain, that, after understanding the invention, various changes and modifications may be made without departing from the spirit and scope of the invention as defined by the appended claims.

We claim:

1. A biologicaly pure culture of a variant of *Bacillus stearothermophilus*, having the identifying characteristics of ATCC No. 39,536, which produces a thermostable amylase having a low calcium ion requirement and active at neutral pHs, when cultivated in a suitable nutrient medium.

2. A thermostable amylase having a low calcium ion requirement as shown in FIGS. 10 and 11 and active at neutral pHs derived from an organism having the identifying characteristics of ATCC No. 59,536 belonging to the species *Bacillus stearothermophilus*.

3. An immobilized enzyme composite comprising the amylase of claim 2 attached to an insoluble carrier.

4. A method of producing a thermostable amylase having a low calcium ion requirement and active at neutral pHs comprising:

(a) culturing a *Bacillus stearothermophilus* organism having the identifying characteristics of ATCC No. 39,536 which produces the thermostable amylase extracellularly, in a suitable nutrient medium; and (b) recovering the amylase.

* * * * *